United States Patent [19]

Schröder et al.

[11] 4,244,960
[45] Jan. 13, 1981

[54] INDANYL DERIVATIVES AND THEIR USE

[75] Inventors: Eberhard Schröder; Clemens Rufer; Irmgard Böttcher; Joachim-Friedrich Kapp, all of Berlin, Fed. Rep. of Germany

[73] Assignee: Schering, Aktiengesellschaft, Berlin and Bergkamen, Fed. Rep. of Germany

[21] Appl. No.: 61,779

[22] Filed: Jul. 27, 1979

[30] Foreign Application Priority Data

Jul. 27, 1978 [DE] Fed. Rep. of Germany ....... 2833202
Jun. 11, 1979 [DE] Fed. Rep. of Germany ....... 2923937

[51] Int. Cl.³ .................. A61K 31/44; C07D 213/63; C07D 213/70; A61K 31/18
[52] U.S. Cl. .................................. 424/263; 424/321; 546/293; 564/97; 564/99; 71/94; 71/98
[58] Field of Search ...................... 260/556 A, 556 F; 546/293; 424/263, 321

[56] References Cited

U.S. PATENT DOCUMENTS 2,921,958   1/1960   Feichtinger ............... 260/556 A
3,288,852  11/1966   Dunbar .................... 260/556 A Primary Examiner—Alan L. Rotman
Assistant Examiner—Robert T. Bond
Attorney, Agent, or Firm—Millen & White

[57] ABSTRACT

Indanyl derivatives of the formula

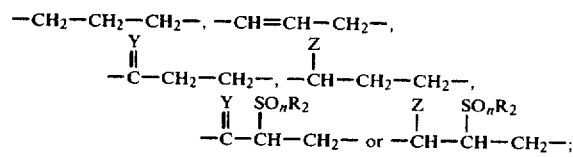

wherein AR is phenyl, pyridyl, or phenyl or pyridyl substituted by halogen, alkyl of 1–4 carbon atoms or trifluoromethyl; X is oxygen or a sulfur; $R_1$ is alkyl of 1–4 carbon atoms or alkyl of 1–4 carbon atoms substituted by fluorine or chlorine; A is $$-CH_2-CH_2-CH_2-,\ -CH=CH-CH_2-,$$
$$\underset{\underset{\parallel}{Y}}{-C}-CH_2-CH_2-,\ \underset{\underset{|}{Z}}{-CH}-CH_2-CH_2-,$$
$$\underset{\underset{|}{SO_nR_2}}{\underset{\underset{\parallel}{Y}}{-C}}-CH-CH_2-\ \text{or}\ \underset{\underset{|}{SO_nR_2}}{\underset{\underset{|}{Z}}{-CH}}-CH-CH_2-;$$

Y is oxo, oximino, $C_{1-4}$-alkoximino of 1–4 carbon atoms, phenylhydrazono or p-toluenesulfonylhydrazono; n is 0, 1 or 2; $R_2$ is alkyl of 1–4 carbon atoms, phenyl or phenyl substituted by halogen, alkyl of 1–4 carbon atoms, nitro or carboxy; Z is hydroxy, acyloxy of 1 to 6 carbon atoms, $R_1SO_3-$ amino, acylamino of 1 to 6 carbon atoms, $R_1SO_2NH-$ or cyano, and V is hydrogen, acyl of 1 to 6 carbon atoms or $R_1SO_2-$, and the salts thereof with physiologically acceptable bases or acids have valuable pharmacological and herbicidal activity.

73 Claims, No Drawings

INDANYL DERIVATIVES AND THEIR USE

The present invention relates to novel indanyl derivatives having herbicidal and pharmacological activity.

SUMMARY OF THE INVENTION

It is an object of this invention to provide new indanyl derivatives having, e.g., pharmacological activity, as well as methods of using such derivatives.

Upon further study of the specification and appended claims, further objects and advantages of this invention will become apparent to those skilled in the art.

These and other objects have been attained by providing new indanyl derivatives of formula I

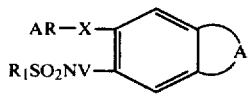
(I)

wherein AR is phenyl, pyridyl, or phenyl or pyridyl substituted by halogen, alkyl of 1–4 carbon atoms or trifluoromethyl; X is oxygen or sulfur; $R_1$ is alkyl of 1–4 carbon atoms or alkyl of 1–4 carbon atoms substituted by fluorine or chlorine; A is

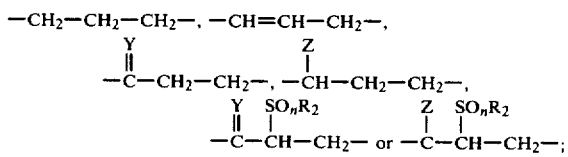

Y is oxo, oximino, $C_{1-4}$-alkoximino of 1–4 carbon atoms, phenylhydrazono or p-tolunesulfonylhydrazono; n is 0, 1 or 2; and $R_2$ is alkyl of 1–4 carbon atoms, phenyl or phenyl substituted by halogen, alkyl of 1–4 carbon atoms, nitro or carboxy; Z is hydroxy, acyloxy of 1 to 6 carbon atoms, $R_1SO_3$— wherein $R_1$ has the meaning given above, amino, acylamino of 1 to 6 carbon atoms, $R_1SO_2NH$— wherein $R_1$ has the meaning given above, or cyano, V is hydrogen, acyl of 1 to 6 carbon atoms or $R_1SO_2$— wherein $R_1$ has the meaning given above, and the salts thereof with physiologically acceptable bases or acids.

DETAILED DISCUSSION

In the indanyl derivatives of formula I, the substituent AR may be phenyl or pyridyl both of which can optionally be substituted by 1–3 halogen atoms (preferably fluorine atoms, chlorine atoms, or bromine atoms), by 1–3 alkyl groups each containing 1–4 carbon atoms (e.g., ethyl, propyl, isopropyl or especially methyl), by 1–3 trifluoromethyl groups or by combinations thereof. Suitable substituents AR include, for example, 2-, 3-, or 4-fluorophenyl, 2-, 3-, or 4-chlorophenyl, 2-, 3-, or 4-bromophenyl, 2,3-, 2,4-, 2,6-, 3,4- or 3,5-difluorophenyl, 2,3-, 2,4-, 2,6-, 3,4- or 3,5-dichlorophenyl, 2-, 3- or 4-methylphenyl, 2-, 3- or 4-isopropylphenyl, 2,3-, 2,4-, 2,6-, 3,4- or 3,5-dimethylphenyl, 2-chloro-4-fluorophenyl, 2-, 3- or 4-trifluoromethylphenyl, 2-chloro-3-methylphenyl, 3-chloro-2-methylphenyl, 2-chloro-4-methylphenyl, 4-chloro-2-methylphenyl, 2-chloro-6-methylphenyl, 2,3-dichloro-4-methylphenyl, 4-chloro-2-fluorophenyl, 2,4,6-trichlorophenyl, 2-fluoro-3-trifluoromethylphenyl, 2-fluoro-4-trifluoromethylphenyl, 3-fluoro-2-trifluoromethylphenyl, 4-fluoro-2-trimethyl- phenyl, 2-fluoro-6-trifluoromethylphenyl, 2-pyridyl, 3-pyridyl, 4-pyridyl, 5-chloro-2-pyridyl, 4-chloro-3-pyridyl, 6-fluoro-3-pyridyl and the like.

Suitable $R_1$ groups of the indanyl derivatives of formula I include, for example, methyl, ethyl, propyl, isopropyl, butyl, chloromethyl, fluoromethyl, trifluoromethyl and the like. The halogenated alkyl groups can contain 1–3 halo atoms.

Suitable $C_{1-4}$ alkoximino groups as Y include, e.g., methoximino, ethoximino, propoximino, butoximino and the like.

Suitable acyl, acyloxy or acylamino groups of Z and acyl groups of V include carboxylic acid acyl radicals.

Suitable $R_2$ groups include, e.g., methyl, ethyl, propyl, isopropyl, butyl, phenyl, 3-nitrophenyl, 2-carboxyphenyl, 4-fluorophenyl, 2-methylphenyl, 2-chlorophenyl and the like. Substituted phenyl groups may contain 1–3 substituents in any combination.

In formula I, the A groups

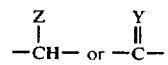

can be in the meta- or para-positions with respect to the substituent AR-X of the phenyl nucleus. Particularly preferred compounds are those wherein (a) AR is phenyl or phenyl substituted by halogen, alkyl of 1–4 carbon atoms or trifluoromethyl; and A is —$CH_2CH_2CH_2$—;

(b) AR is phenyl or phenyl mono- or disubstituted by fluorine or chlorine;

(c) $R_1$ is methyl in conjunction with (a) or (b);

(d) Y is oxo in conjunction with (a), (b) or (c).

The novel indanyl derivatives of formula I can be prepared according to conventional methods. For example, they may be prepared by (a) condensing a compound of formula II

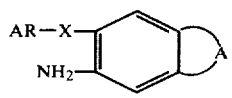
(II)

wherein AR, X and A are as defined above, with a sulfonic acid derivative of formula III

 (III)

wherein $R_1$ is as defined above and W is halogen or $R_1SO_2O$—;

(b) to prepare the indan derivatives wherein A is —$COCH_2CH_2$—, oxidizing an indan derivative of formula I wherein A is —$CH_2CH_2CH_2$—;

(c) to prepare the indan derivatives wherein A is

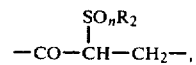

reacting an indan derivative of formula I wherein A is —$COCH_2CH_2$—, in the presence of a strong base, with a disulfide of formula IV

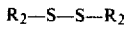 (IV)

wherein $R_2$ is as defined above, and optionally, oxidizing the thus-obtained thio compounds of formula I to the corresponding sulfoxides or sulfones;

(d) to prepare the indan derivatives wherein Y is oximino, alkoximino of 1–4 carbon atoms, phenylhydrazono or p-toluenesulfonylhydrazono, condensing an indan derivative of formula I wherein Y is oxo with the corresponding oxime or hydrazone;

(e) to prepare the indan derivatives wherein Z is hydroxy or amino, reducing an indan derivative of formula I wherein A is

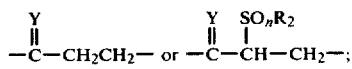

or (f) to prepare the indan derivatives wherein A is —CH═CH—CH$_2$—, dehydrating an indan derivative of formula I wherein A is

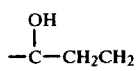

and optionally acylating the compounds wherein V is hydrogen and/or Z is hydroxy or amino.

The condensation of the compounds of formula II with the sulfonic acid chlorides or anhydrides of formula III according to process variation (a) takes place under conditions known per se, for example by reacting the sulfonic acid chlorides with the compounds of formula II in the presence of alkaline catalysts, such as sodium carbonate, sodium hydroxide, potassium bicarbonate, potassium carbonate, pyridine, lutidine, or collidine.

The oxidation of the methylene groups to the corresponding carbonyl groups according to process variation (b) can be effected, for example, with potassium permanganate in an alkaline, neutral or weakly acidic aqueous solution or by using a solution of chromium(VI) oxide in glacial acetic acid at a temperature of −10° C. to 110° C.

Process variation (c) can be conducted, for example, by reacting the starting compounds in an aprotic solvent (pyridine, dimethylformamide, hexamethylphosphoric triamide, dioxane, tetrahydrofuran, etc.) with an alkali metal hydride or alkali metal amide (e.g. sodium hydride or lithiumdiisopropylamide) and treating the thus-obtained reaction mixture with the desired disulfide. This reaction is preferably carried out at a reaction temperature of −60° C. to +20° C.

The optionally following oxidation of the thio compounds to the sulfoxides or sulfones of formula I takes place according to conventional operating methods. For example, suitable oxidizing agents include, for example, peracids, e.g. peracetic acid, perbenzoic acid or m-chloroperbenzoic acid; hydrogen peroxide; quinones, such as 2,3-dichloro-5,6-dicyanobenzoquinone; tetravalent to heptavalent metal oxides or metallic salts, such as lead (IV) oxide, manganese (IV) oxide, chriomium (VI) oxide, cerium (IV) sulfate, potassium chromate, potassium dichromate, potassium permanganate; or oxidizing halogen compounds, such as iodine, sodium periodate, N-bromosuccinimide, N-chlorosuccinimide or sodium chloride. If hydrogen peroxide or metallic oxides or salts are used for this oxidation, it is advantageous to conduct the oxidation in the presence of acids. Suitable acids include mineral acids, such as hydrogen chloride or sulfuric acid, or lower carboxylic acids, such as acetic acid or propionic acid. Suitable solvents for this reaction include protonic as well as aprotic inert solvents. Examples of suitable solvents are lower carboxylic acids, such as acetic acid or propionic acid; tertiary alcohols, such as tert-butanol; ketones, such as acetone, methyl ethyl ketone or cyclohexanone; ethers, such as diethyl ether, diisopropyl ether, tetrahydrofuran, dioxane or glycol dimethyl ether; hydrocarbons, such as benzene or toluene; or chlorinated hydrocarbons, such as methylene chloride, chloroform, carbon tetrachloride, tetrachloroethane or chlorobenzene. For the preparation of sulfones of formula I, acetic acid is preferably utilized as the solvent. The preparation of sulfoxides takes place preferably in acetone as the solvent.

Process variation (d) is preferably accomplished in a polar solvent (e.g. a lower alcohol, such as methanol, ethanol, or isopropanol, or a lower carboxylic acid, such as acetic acid) at a reaction temperature of from −10° to 110° C.

Process version (e) can be conducted by reducing the starting compounds with complex metal hydrides, e.g. sodium borohydride (in a lower alcohol, such as methanol, ethanol, or isopropanol as the solvent), optionally with the addition of boron trifluoride or trifluoroacetic acid or lithium aluminum hydride (in a polar ether, such as tetrahydrofuran or dioxane as the solvent). On the other hand, this variation can also be conducted by hydrogenating the starting compounds in the presence of a hydrogenation catalyst (Raney nickel, platinum oxide, palladium-animal charcoal, etc.) with hydrogen at a pressure of 1–150 atmospheres.

Process variation (f) is carried out under the conditions customarily employed for dehydration. Suitable methods include, for example, dehydrating by reacting the compounds with acids (p-toluenesulfonic acid, sulfuric acid, polyphosphoric acid, etc.) or dehydrating agents (silica gel, phosphorus pentoxide, etc.) in inert solvents (lower ketones, such as acetone; ethers, such as tetrahydrofuran or dioxane; or aromatic hydrocarbons, such as benzene, toluene or xylene).

The starting compounds for the processes of this invention are known or can be prepared by conventional methods.

Thus, it is possible, for example to prepare the compounds of formula II by condensing compounds of formula IV with compounds of formula III and subsequently reducing the thus-obtained nitro compounds of formula V:

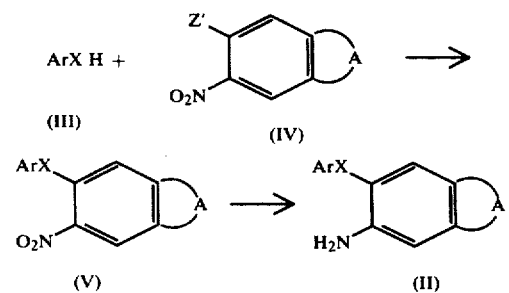

wherein ArX and A are as defined above and Z' is chlorine, bromine or iodine.

The conditions under which these starting compounds can be synthesized are described below, using selected representatives as typical examples.

The indanyl derivatives of formula I are useful as herbicides and pharmacologically active compounds distinguished, for example, by analgesic, antipyretic, thrombocyte-aggregation-inhibiting, diuretic and, especially, antiphlogistic activities. A special distinguishing feature of these compounds as pharmaceuticals is that they display an extensive dissociation between their therapeutic activities and the attendant undesirable side effects (especially ulcerogenic activity). Moreover, it is remarkable that these compounds hardly inhibit the synthesis of prostaglandins.

The pharmacological activities of these compounds can be demonstrated by fully conventional pharmacological screening tests. For example, their antiphlogistic efficacy can be shown by the conventional adjuvant arthritis test which is conducted as follows:

Female and male rats of the Lewis strain (LEW) are used in a weight range of 110-190 g. The animals receive drinking water and "Altromin" pressed feed ad libitum. Ten rats are employed for each dosage group. The irritant is Mycobacterium butyricum (Difko, Detroit). A suspension of 0.5 mg of Mycobacterium butyricum in 0.1 ml of thinly fluid paraffin (DAB [German Pharmacopoeia] 7) is injected in the subplantar region of the right hind paw. The test substances are orally administered, starting with the 11th day of the experiment, daily over a period of 4 days. The compounds are applied as a clear aqueous solution or as a crystalline suspension with the addition of Myrj 53 (85 mg %) in an isotonic sodium chloride solution.

TEST SETUP:

The rats are divided into various groups as uniformly as possible with respect to their body weight. After measuring the volume of the right hind paw by plethysmography, 0.1 ml of adjuvant is injected in the subplantar region of the right hind paw. The right hind paws are measured starting with the 14th day of the experiment until the end of the experiment. The duration of the experiment is 3 weeks. The healing of the hind paws attained at the given dosage is determined.

A frequent complication in therapy with non steroidal anti-inflammatory agents is the occurrence of stomach ulcerations. This side effect can be proven by animal experiments, determining the number of lesions occurring at a given dosage and their total area. The ulcer test is conducted as follows.

Male Wistar rats (SPF) are utilized. The animals have a weight range of 130±10 g. The animals are put on a fast 16 hours before the beginning of the experiment; they receive water ad libitum. Five animals are used per dosage. The compounds are orally administered once, dissolved in sodium chloride or as a crystalline suspension with the addition of 85 mg % Myrj 53. Three hours after application of the compound, 1 ml of a 3% solution of the diphenyl pure blue dye is injected intravenously, and the animal is sacrificed. The stomach is resected and examined under a microscope to determine the number and total area of epithelial lesions and ulcera made prominent by dye enrichment.

The following table contains the results obtained in these tests for the compounds of this invention as compared with the previously known indomethacin (compound 1). These results demonstrate the superiority of the compounds of the present invention—especially with respect to their superior dissociation between anti-inflammatory and ulcerogenic activities.

| | | | Adjuvant Arthritis Test % healing | | Ulcus Test | | |
| | | Compound mg./kg. | | | Compound in mg./kg. | Lesions | |
| No. | Compound | Animal | Right Paw | Left Paw | Animal | Number | Area |
| --- | --- | --- | --- | --- | --- | --- | --- |
| 1 | Indomethacin | 4 × 4 mg. | 50 | 70 | 8 mg. | 9.6 | 6.3 |
| 2 | N-(6-Phenoxy-5-indanyl)methanesulfonamide | 4 × 30 mg. | 54 | 74 | 200 mg. | 0.4 | 0.2 |
| 3 | N-(6-Phenoxy-5-indanyl)trifluoromethanesulfonamide | 4 × 30 mg. | 47 | 81 | 200 mg. | 0.4 | 0.2 |
| 4 | N-[6-(4-Fluorophenoxy)-5-indanyl]methanesulfonamide | 4 × 30 mg. | 53 | 76 | 200 mg. | 0.2 | 0.1 |
| 5 | N-[6-(4-Chlorophenoxy)-5-indanyl]methanesulfonamide | 4 × 30 mg. | 61 | 86 | 200 mg. | 1.4 | 0.7 |
| 6 | N-[6-(4-Chloro-2-methylphenoxy)-5-indanyl]methanesulfonamide | 4 × 30 mg. | 48 | 57 | 200 mg. | 0.2 | 0.1 |
| 7 | N-[6-(2-Chlorophenoxy)-5-indanyl]methanesulfonamide | 4 × 30 mg. | 51 | 72 | 200 mg. | 0.2 | 0.1 |
| 8 | N-(6-Phenylthio-5-indanyl)methanesulfonamide | 4 × 30 mg. | 46 | 75 | 200 mg. | 2.0 | 1.0 |
| 9 | N-[6-(2-Pyridylthio)-5-indanyl]methanesulfonamide | 4 × 30 mg. | 54 | 71 | 200 mg. | 0.4 | 0.2 |

-continued

| No. | Compound | Compound mg./kg. Animal | Adjuvant Arthritis Test % healing | | Ulcus Test | | |
|---|---|---|---|---|---|---|---|
| | | | Right Paw | Left Paw | Compound in mg./kg. Animal | Lesions | |
| | | | | | | Number | Area |
| 10 | 5-Methylsulfonyl-amino-6-phenoxy-1-indanone | 4 × 30 mg. | 55 | 69 | 200 mg. | 0.2 | 0.1 |
| 11 | N-(5-Phenoxy-6-indenyl)methane-sulfonamide | 4 × 30 mg. | 43 | 80 | 200 mg. | 0.3 | 0.1 |
| 12 | 5-Methanesulf-onylamino-6-phenoxy-2-phenylsulfinyl-1-indanone | 4 × 30 mg. | 50 | 78 | 200 mg. | 0.1 | 0.1 |

Thus, the novel compounds are suitable, in combination with the excipients customary in galenic pharmacy, for the treatment of, for instance, acute and chronic polyarthritis, neurodermitis, bronchial asthma, hay fever, and others, in patients, e.g., mammals including humans.

The drug specialties are prepared in the usual way by converting the active agents with suitable additives, carrier materials, and flavor-ameliorating agents into the desired forms of administration, such as tablets, dragees, capsules, solutions, inhalants, etc. In the thus-formulated medicinal agents, the effective agent concentration is dependent on the compound used and the form of application and can be easily determined by routine, e.g., clinical tests under conventional considerations.

The pharmacologically active compounds of formula I can be processed in accordance with conventional methods of galenic pharmacy to provide medicinal agents, especially for oral administration. Conventional excipients are pharmaceutically acceptable organic or inorganic carrier substances suitable for parenteral, enteral or topical application which do not deleteriously react with the active compounds. Suitable pharmaceutically acceptable carriers include but are not limited to water, salt solutions, alcohols, vegetable oils, polyethylene glycols, gelatine, lactose, amylose, magnesium stearate, talc, silicic acid, viscous paraffin, perfume oil, fatty acid monoglycerides and diglycerides, pentaerythritol fatty acid esters, hydroxymethylcellulose, polyvinyl pyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, coloring, flavoring and/or aromatic substances and the like which do not deleteriously react with the active compounds.

For parenteral application, particularly suitable are solutions, preferably oily or aqueous solutions, as well as suspensions, emulsions, or implants, including suppositories. Ampoules are convenient unit dosages.

For enteral application, particularly suitable are tablets, dragees, or capsules having talc and/or a carbohydrate carrier or binder or the like, the carrier preferably being lactose and/or corn starch and/or potato starch. A syrup, elixir or the like can be used wherein a sweetened vehicle is employed. Sustained release compositions can be formulated including those wherein the active compound is protected with differentially degradable coatings, e.g., by microencapsulation, multiple coatings, etc.

For topical applications, the compounds are employed as non-sprayable forms, viscous to semi-solid or solid forms comprising a carrier indigenous to topical application and having a dynamic viscosity preferably greater than water. Suitable formulations include but are not limited to solutions, suspensions, lotions, emulsions, creams, ointments, plasters, powders, linaments, salves, aerosols, etc., which are, if desired, sterilized or mixed with auxiliary agents, e.g., preservatives, stabilizers, wetting agents, buffers, or salts for influencing osmotic pressure, etc. For topical application, also suitable are sprayable aerosol preparations wherein the active ingredient, preferably in combination with a solid or liquid inert carrier material, is packaged in a squeeze bottle or in admixture with a pressurized volatile, normally gaseous propellant, e.g., a freon. Usually, the active compounds of the invention are incorporated in topical formulations in a concentration of about 0.001 to 1 wt. %.

Especially suitable for oral administration are tablets, dragees, and capsules containing, for example, 1–250 mg of active ingredient and 50 mg to 2 g of a pharmacologically inert vehicle, e.g. lactose, amylose, talc, gelatin, magnesium stearate, and similar compounds, as well as the usual additives.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

(a) 2.1 g. of 5-bromo-6-nitrodinane, 0.75 g. of copper(I) chloride, 17.3 g. of potassium carbonate, and 18.4 g. of phenol in 200 ml. of absolute pyridine are refluxed for 3 hours. The mixture is concentrated under vacuum, the residue is combined with chloroform, and the mixture is vacuum-filtered from the insoluble matter. The mother liquor is extracted respectively three times with 1 N sodium hydroxide solution and 1 N hydrochloric acid and concentrated under vacuum. After distillation under vacuum, 11.5 g. of 5-nitro-6-phenoxyindane is obtained, b.p.$_{0.03}$ 163°–165°. Melting point: 41° (hexane).

(b) A solution of 17.7 g. of 5-nitro-6-phenoxyindane in 500 ml. of methanol is hydrogenated in the presence of 15 g. of Raney nickel within 4 hours at 70 atm. The product is filtered off from the catalyst, concentrated under vacuum, and recrystallized from aqueous ethanol, thus obtaining 12.9 g. of 6-phenoxy-5-indanylamine, m.p. 62°.

(c) At 0° 4 ml. of methanesulfochloride is added dropwise within 10 minutes to a solution of 7.8 g. of 6-phenoxy-5-indanylamine in 50 ml. of absolute pyridine. The mixture is stirred for 3 hours at 0° and for 16 hours at room temperature and concentrated under vacuum. The residue is taken up in chloroform, extracted three times with 1 N hydrochloric acid, and concentrated under vacuum. The mixture is recrystallized from aqueous ethanol, thus obtaining 9.5 g. of N-(6-phenoxy-5-indanyl)methanesulfonamide, m.p. 130°.

EXAMPLE 2

Analogously to Example 1, the following products are obtained, starting with 5-bromo-6-nitroindan and 4-chlorophenol:
(a) 5-(4-chlorophenoxy)-6-nitroindan, b.p.$_{0.03}$ 165°–168°, m.p. 67° (hexane)
(b) 6-(4-chlorophenoxy)-5-indanylamine, m.p. 66°
(c) N-[6-(4-chlorophenoxy)-5-indanyl]methanesulfonamide, m.p. 57°

EXAMPLE 3

Analogously to Example 1, the following products are obtained, starting with 5-bromo-6-nitroindan and p-cresol:
(a) 5-nitro-6-(4-tolyloxy)indan, b.p.$_{0.03}$ 168°–173° and m.p. 58° (hexane)
(b) 6-(4-tolyloxy)-5-indanylamine as an oil
(c) N-[6-(4-tolyloxy)-5-indanyl]methanesulfonamide, m.p. 139°

EXAMPLE 4

Analogously to Example 1, the following compounds are produced, starting with 5-bromo-6-nitroindan and 4-fluorophenol:
(a) 5-(4-fluorophenoxy)-6-nitroindan, and m.p. 63° (hexane)
(b) 6-(4-fluorophenoxy)-5-indanylamine, m.p. 72°
(c) N-[6-(4-fluorophenoxy)-5-indanyl]methanesulfonamide, m.p. 100°

EXAMPLE 5

Analogously to Example 1, the following compounds are obtained, starting with 5-bromo-6-nitroindan and 3-trifluoromethylphenol:
(a) 6-nitro-5-(3-trifluoromethylphenoxy)indan, b.p.$_{0.03}$ 155°–163° and m.p. 69° (hexane)
(b) 6-(3-trifluoromethylphenoxy)-5-indanylamine as an oil
(c) N-[6-(3-trifluoromethylphenoxy)-5-indanyl]methanesulfonamide, m.p. 81°

EXAMPLE 6

Analogously to Example 1, the following products are produced, starting with 5-bromo-6-nitroindan and 4-chloro-2-methylphenol:
(a) 5-(4-chloro-2-methylphenoxy)-6-nitroindan, b.p.$_{0.03}$ 187°–190° and m.p. 61° (hexane)
(b) 6-(4-chloro-2-methylphenoxy)-5-indanylamine as an oil
(c) N-[6-(4-chloro-2-methylphenoxy)-5-indanyl]methanesulfonamide, m.p. 116°

EXAMPLE 7

Analogously to Example 1, the following products are obtained, starting with 5-bromo-6-nitroindan and 2-chlorophenol:
(a) 5-(2-chlorophenoxy)-6-nitroindan, b.p.$_{0.03}$ 175°–178°
(b) 6-(2-chlorophenoxy)-5-indanylamine as an oil
(c) N-[6-(2-chlorophenoxy)-5-indanyl]methanesulfonamide, m.p. 120°

EXAMPLE 8

Analogously to Example 1, the following compounds are obtained, starting with 5-bromo-6-nitroindan and 3-chlorophenol:
(a) 5-(3-chlorophenoxy)-6-nitroindan, b.p.$_{0.03}$ 176°–182°
(b) 6-(3-chlorophenoxy)-5-indanylamine as an oil
(c) N-[6-(3-chlorophenoxy)-5-indanyl]methanesulfonamide, m.p. 109°–111°

EXAMPLE 9

Analogously to Example 1, the following products are obtained, starting with 5-bromo-6-nitroindan and 2-fluorophenol:
(a) 5-(2-fluorophenoxy)-6-nitroindan, b.p.$_{0.03}$ 155°–165° and m.p. 47°
(b) 6-(2-fluorophenoxy)-5-indanylamine as an oil
(c) N-[6-(2-fluorophenoxy)-5-indanyl]methanesulfonamide, m.p. 78°

EXAMPLE 10

Analogously to Example 1, the following compounds are produced, starting with 5-bromo-6-nitroindan and 2-chloro-4-fluorophenol:
(a) 5-(2-chloro-4-fluorophenoxy)-6-nitroindan as an oil
(b) 6-(2-chloro-4-fluorophenoxy)-5-indanylamine, m.p. 63°
(c) N-[6-(2-chloro-4-fluorophenoxy)-5-indanyl]methanesulfonamide, m.p. 90°

EXAMPLE 11

Analogously to Example 1, the following compounds are obtained, starting with 5-bromo-6-nitroindan and 3,4-dichlorophenol:
(a) 5-(3,4-dichlorophenoxy)-6-nitroindan after silica gel column purification (system: tetrachloromethane/ethyl acetate 30:1) as an oil
(b) 6-(3,4-dichlorophenoxy)-5-indanylamine, m.p. 84°
(c) N-[6-(3,4-dichlorophenoxy)-5-indanyl]methanesulfonamide, m.p. 135°

EXAMPLE 12

Analogously to Example 1, the following products are prepared, starting with 5-bromo-6-nitroindan and 4-bromophenol:
(a) 5-(4-bromophenoxy)-6-nitroindan, b.p.$_{0.03}$ 183°–185°
(b) 6-(4-bromophenoxy)-5-indanylamine, m.p. 66°
(c) N-[6-(4-bromophenoxy)-5-indanyl]methanesulfonamide, m.p. 118°

EXAMPLE 13

Analogously to Example 1, the following compounds are produced, starting with 5-bromo-6-nitroindan and 2,4-dichlorophenol:

(a) 5-(2,4-dichlorophenoxy)-6-nitroindan, purification by way of a silica gel column (system: tetrachloromethane/ethyl acetate 30:1), as an oil
(b) 6-(2,4-dichlorophenoxy)-5-indanylamine as an oil
(c) N-[6-(2,4-dichlorophenoxy)-5-indanyl]methanesulfonamide, m.p. 90°

EXAMPLE 14

Analogously to Example 1, the following products are prepared, starting with 5-bromo-6-nitroindan and o-cresol:
(a) 5-nitro-6-(2-tolyloxy)indan, b.p.$_{0.05}$ 163°–166°
(b) 6-(2-tolyloxy)-5-indanylamine as an oil
(c) N-[6-(2-tolyloxy)-5-indanyl]methanesulfonamide, m.p. 92°

EXAMPLE 15

Analogously to Example 1, the following compounds are obtained, starting with 5-bromo-6-nitroindan and 3-fluorophenol:
(a) 5-(3-fluorophenoxy)-6-nitroindan, b.p. $_{0.03}$ 155°–163°
(b) 6-(3-fluorophenoxy)-5-indanylamine, m.p. 49°
(c) N-[6-(3-fluorophenoxy)-5-indanyl]methanesulfonamide, m.p. 102°

EXAMPLE 16

(a) Under nitrogen, 14.6 g. of 5-bromo-6-nitroindan, 1.2 g. of copper(I) chloride, 12.4 ml. of thiophenol, and 8.4 g. of potassium carbonate are refluxed in 150 ml. of absolute pyridine for 3 hours. The mixture is concentrated under vacuum and worked up as described in Example 1(a). The reaction product is recrystallized from ethyl acetate, thus obtaining 8.1 g. of 5-phenylthio-6-nitroindan, m.p. 112°.

(b) Under boiling heat, 5 g. of Raney nickel is introduced into a solution of 9 g. of 5-phenylthio-6-nitroindan in 160 ml. of ethanol and 6.6 ml. of hydrazine hydrate; the mixture is refluxed for 1¼ hours. The product is filtered off from the catalyst, concentrated until crystallization occurs, and the product is 7.1 g. of 6-phenylthio-5-indanylamine, m.p. 80°

(c) The thus-obtained product is reacted, as described in Example 1(c), to N-(6-phenylthio-5-indanyl)methanesulfonamide, m.p. 115.5°.

EXAMPLE 17

Analogously to Example 16, starting with 5-brom-6-nitroindan and 4-tert.-butylbenzenethiol, the following compounds are obtained:
(a) 5-(4-tert.-butylphenylthio)-6-nitroindan, m.p. 94°
(b) 6-(4-tert.-butylphenylthio)-5-indanylamine, m.p. 92°
(c) N-[6-(4-tert.-butylphenylthio)-5-indanyl]methanesulfonamide, m.p. 116°

EXAMPLE 18

Analogously to Example 16, the following compounds are produced, starting with 5-bromo-6-nitroindan and 4-fluorobenzenethiol:
(a) 5-(4-fluorophenylthio)-6-nitroindan, m.p. 106°
(b) 6-(4-fluorophenylthio)-5-indanylamine, m.p. 60°
(c) N-[6-(4-fluorophenylthio)-5-indanyl]methanesulfonamide, m.p. 139°

EXAMPLE 19

(a) 2.4 g. of 5-bromo-6-nitroindan, 2.25 g. of potassium tert.-butylate, and 2.9 g. of 4-chlorobenzenethiol are heated in 30 ml. of absolute dimethylformamide under nitrogen to 60° for 3 hours. The mixture is concentrated under vacuum, combined with ethyl acetate, and extracted three times with 2 N sodium hydroxide solution. The mixture is again concentrated, and the residue is purified on a silica gel column (system: tetrachloromethane/ethyl acetate 25:1) and recrystallized from ethanol, yielding 1.2 g. of 5-(4-chlorophenylthio)-6-nitroindan, m.p. 118°.

(b) Analogously to Example 16(b), the following product is obtained therefrom: 6-(4-chlorophenylthio)-5-indanylamine, m.p. 63°.

(c) Analogously to Example 1(c), the following product is prepared therefrom: N-[6-(4-chlorophenylthio)-5-indanyl]methanesulfonamide, m.p. 109°.

EXAMPLE 20

(a) 4.8 g. of 5-bromo-6-nitroindan, 4.5 g. of potassium tert.-butylate, 4.4 g. of 2-pyridinethiol are heated in 50 ml. of absolute dimethylformamide for 3 hours under nitrogen to 80°. The mixture is concentrated under vacuum; the residue is combined with ethyl acetate and extracted four times with water. The ethyl acetate phase is concentrated, and the residue is purified on a silica gel column (system: cyclohexane/ethyl acetate 4:1). After crystallization from ethanol, 3.3 g. of 5-nitro-6-(2-pyridylthio)indan is obtained, m.p. 74°.

(b) Analogously to Example 16(b), the following product is obtained therefrom: 6-(2-pyridylthio)-5-indanylamine, m.p. 126°.

(c) Analogously to Example 1(c), the ensuing product is: N-[6-(2-pyridylthio)-5-indanyl]methanesulfonamide, m.p. 141°.

EXAMPLE 21

(a) Under nitrogen, 7.2 g. of 5-bromo-6-nitroindan and 3.9 g. of 4-pyridinethiol are heated in 120 ml. of dimethyl sulfoxide with 3.6 g. of sodium bicarbonate for 7 hours to 50°. The mixture is concentrated, the residue is dissolved in chloroform/water and extracted three times with water, then concentrated and purified by way of a silica gel column (system: cyclohexane/ethyl acetate 1:1). Crystallization from ethanol yields 2 g. of 5-(4-pyridylthio)-6-nitroindan, m.p. 113°.

(b) Analogously to Example 16(b), the following compound is obtained therefrom: 6-(4-pyridylthio)-5-indanylamine, m.p. 140°.

(c) Analogously to Example 1(c), the following product results: N-[6-(4-pyridylthio)-5-indanyl]methanesulfonamide, m.p. 156°.

EXAMPLE 22

Analogously to Example 1, the following compounds are produced, starting with 5-bromo-6-nitroindan and 3-chloropyridine:
(a) 6-(3-pyridyloxy)-5-nitroindan as an oil
(b) 6-(3-pyridyloxy)-5-indanylamine, m.p. 118°
(c) N-[6-(3-pyridyloxy)-5-indanyl]methanesulfonamide, m.p. 126°.

EXAMPLE 23

1.1 g. of 6-phenoxy-5-indanylamine is dissolved in 15 ml. of absolute pyridine and combined at 0° within 10 minutes with 1.6 ml. of trifluoromethanesulfonic anhydride in 5 ml. of absolute benzene. The mixture is agitated for 3 hours at 0° and for 16 hours at room temperature, concentrated under vacuum, and the residue is taken up in chloroform and extracted three times with 1

N hydrochloric acid. The chloroform phase is then concentrated under vacuum, the residue is purified on a silica gel column (system: chloroform) and recrystallized from hexane, thus obtaining 0.74 g. of N-(6-phenoxy-5-indanyl)-trifluoromethanesulfonamide, m.p. 90°.

EXAMPLE 24

Analogously to Example 23, the following compound is obtained from 6-phenylthio-5-indanylamine:
N-(6-phenylthio-5-indanyl)trifluoromethanesulfonamide, m.p. 67°.

EXAMPLE 25

Analogously to Example 23, the following compound is obtained from 6-(4-fluorophenoxy)-5-indanylamine:
N-[6-(4-fluorophenoxy)-5-indanyl]trifluoromethanesulfonamide, m.p. 123°.

EXAMPLE 26

Analogously to Example 23, the following compound is produced from 4-chlorophenoxy-5-indanylamine:
N-[6-(4-chlorophenoxy)-5-indanyl]trifluoromethanesulfonamide, m.p. 139°.

EXAMPLE 27

Analogously to Example 23, the following product is prepared from 6-phenoxy-5-indanylamine with chloromethanesulfonic anhydride: N-(6-phenoxy-5-indanyl)chloromethanesulfonamide, m.p. 73°.

EXAMPLE 28

Analogously to Example 23, the following compound is produced from 6-phenoxy-5-indanylamine with ethanesulfonic anhydride: N-(6-phenoxy-5-indanyl)ethanesulfonamide, m.p. 89°.

EXAMPLE 29

(a) 11 g. of 5-nitro-6-phenoxyindan and 17.3 g. of bis(dimethylamino) tert.-butoxymethane are heated to 155° within 60 minutes and maintained at this temperature for 60 minutes, during which step tert.-butanol is distilled off. The mixture is then concentrated under vacuum, combined with 50 ml. of ethanol, and vacuum-filtered, thus obtaining 9.2 g. of 1-dimethylaminomethylene-5-nitro-6-phenoxyindan, m.p. 97°.

(b) 6.2 g. of this enamine is dissolved in 100 ml. of chloroform and ozonized at −35°. Filtration over 30 g. of silica gel with chloroform, concentration, and crystallization from 30 ml. of ethanol yield 3.8 g. of 5-nitro-6-phenoxy-1-indanone, m.p. 105°.

(c) 1.58 g. of this nitroketone is dissolved in 20 ml. of ethanol and 10 ml. of dioxane. The solution is combined with 0.74 g. of hydrazine hydrate and, at 35°, about 1.5 g. of Raney nickel (made into a slurry with ethanol) is added in incremental portions. After refluxing for 60 minutes, the reaction mixture is cooled, filtered, and concentrated. Recrystalization from ethanol yields 1.22 g. of 5-amino-6-phenoxy-1-indanone, m.p. 170°.

(d) 1.2 g. of this aminoketone is dissolved in 12 ml. of pyridine at 0°; 0,5 g of methanesulfochloride is added dropwise and the mixture is stirred for 6 hours at 0° and concentrated under vacuum, the residue is combined with ice water, and vacuum filtered. The precipitate is dissolved in dilute sodium hydroxide solution, and the filtered solution is acidified with hydrochloric acid. Vacuum-filtering and recrystallization from ethanol yield 1.35 g. of 5-methylsulfonylamino-6-phenoxy-1-indanone, m.p. 175°.

EXAMPLE 30

Analogously to Example 29, the following compounds are obtained, starting with 6-(4-chlorophenoxy)-5-nitroindan:
(a) 6-(4-chlorophenoxy)-1-dimethylaminomethylene-5-nitroindan, m.p. 117°
(b) 6-(4-chlorophenoxy)-5-nitro-1-indanone, m.p. 131°
(c) 5-amino-6-(4-chlorophenoxy)-1-indanone, m.p. 169°
(d) 6-(4-chlorophenoxy)-5-methylsulfonylamino-1-indanone, m.p. 185°.

EXAMPLE 31

Analogously to Example 29, the following compounds are produced, starting with 6-(4-fluorophenoxy)-5-nitroindan:
(a) 1-dimethylaminomethylene-6-(4-fluorophenoxy)-5-nitroindan, m.p. 128°
(b) 6-(4-fluorophenoxy)-5-nitro-1-indanone, m.p. 150°
(c) 5-amino-6-(4-fluorophenoxy)-1-indanone, m.p. 167°
(d) 6-(4-fluorophenoxy)-5-methylsulfonylamino-1-indanone, m.p. 144°.

EXAMPLE 32

Analogously to Example 29, the following compounds are produced, starting with 6-(3-chlorophenoxy)-5-nitroindan:
(a) 6-(3-chlorophenoxy)-1-dimethylaminomethylene-5-nitroindan, m.p. 78°
(b) 6-(3-chlorophenoxy)-5-nitro-1-indanone, m.p. 92°
(c) 5-amino-6-(3-chlorophenoxy)-1-indanone, m.p. 162°
(d) 6-(3-chlorophenoxy)-5-methylsulfonylamino-1-indanone, m.p. 129°.

EXAMPLE 33

Analogously to Example 29, the following products are prepared, starting with 6-(2-fluorophenoxy)-5-nitroindan:
(a) 1-dimethylaminomethylene-6-(2-fluorophenoxy)-5-nitroindan, m.p. 122°
(b) 6-(2-fluorophenoxy)-5-nitro-1-indanone, m.p. 104°
(c) 5-amino-6-(2-fluorophenoxy)-1-indanone, m.p. 164°
(d) 6-(2-fluorophenoxy)-5-methylsulfonylamino-1-indanone, m.p. 119°.

EXAMPLE 34

3.17 g. of 5-methylsulfonylamino-6-phenoxy-1-indanone is combined in pyrindine at −40° with 27 ml. of a 10% solution of lithium diisopropylamide in hexane. After 20 minutes at −35°, 4.4 g. of diphenyl disulfide in 10 ml. of pyridine is added dropwise to the reaction mixture. After 1 hour at −10° and 2 hours at 20°, 10 ml. of 2-propanol is added dropwise. After concentrating the reaction mixture under vacuum, it is taken up in water, filtered, acidified, and extracted with chloroform. Concentration and chromatography of the residue over 240 g. of silica gel with chloroform as the eluting agent, 400 mg. of 5-methylsulfonylamino-6-phenoxy-2,2-bis(phenylthio)-1-indanone, m.p. 162°, is initially obtained, and thereafter 2 g. of 5-methylsulfonylamino-6-phenoxy-2-phenylthio-1-indanone is produced, m.p. 86°.

EXAMPLE 35

1.7 g. of 5-methylsulfonylamino-6-phenoxy-2-phenylthio-1-indanone is dissolved in 20 ml. of methanol and combined at 20° with 4 ml. of a 1 N solution of perselenic acid (literature: J. Drabowicz, M. Mikolajczyk, Synthesis 1978: 758) in methanol. After 30 minutes, 30 ml. of water is added, methanol is removed under vacuum, and the crystallized product is vacuum-filtered, thus obtaining 1.7 g. of 5-methylsulfonylamino-6-phenoxy-2-phenylsulfinyl-1-indanone, m.p. 120°.

EXAMPLE 36

600 mg. of 5-methylsulfonylamino-6-phenoxy-2-phenylthio-1-indanone is maintained for 30 minutes at 90° in 5 ml. of acetic acid with 2 ml. of 30% hydrogen peroxide. The mixture is then cooled to 20°, 15 ml. of ice water is added, and the crystallized product is vacuum-filtered. Recrystallization from ethanol yields 400 mg. of 5-methylsulfonylamino-6-phenoxy-2-phenylsulfonyl-1-indanone, m.p. 180°.

EXAMPLE 37

4.12 g. of 5-methylsulfonylamino-6-phenoxy-1-indanone is dissolved in 45 ml. of methanol and 13 ml. of 1 N sodium hydroxide solution. At 5° 0.98 g. of sodium borohydride is added. After 16 hours at 20°, the mixture is concentrated, combined with ice water, neutralized with hydrochloric acid, and extracted with chloroform. Washing of the chloroform solution with water, concentration, and recrystallization of the residue from toluene yield 3.3 g. of 5-methylsulfonylamino-6-phenoxy-1-indanol, m.p. 96°.

EXAMPLE 38

1.97 g. of 5-methylsulfonylamino-6-phenoxy-1-indanone is boiled for 6 hours in 40 ml. of methanol and 13 ml. of water with 1.1 g. of sodium acetate trihydrate and 1.05 g. of hydroxylamine hydrochloride. Cooling and vacuum-filtering yield 1.8 g. of N-(1-hydroximino-6-phenoxy-5-indanyl)methanesulfonamide, m.p. 216°.

EXAMPLE 39

3.17 g. of 5-methylsulfonylamino-6-phenoxy-1-indanone is treated with methoxamine hydrochloride as described in Example 38, thus obtaining 2.8 g. of N-(1-methoximino-6-phenoxy-5-indanyl)methanesulfonamide, m.p. 178°.

EXAMPLE 40

3.17 g. of 5-methylsulfonylamino-6-phenoxy-1-indanone is agitated at 80° in 80 ml. of methyl glycol with 2 g. of p-toluenesulfonic acid hydrazide with a few drops of hydrochloric acid for 30 minutes. Cooling and vacuum-filtering yield 3.74 g. of N-[1-(4-toluenesulfonylhydrazono)-6-phenoxy-5-indanyl]methanesulfonamide, m.p. 252°.

EXAMPLE 41

3.33 g. of N-(1-hydroximino-6-phenoxy-5-indanyl)methanesulfonamide is hydrogenated in 100 ml. of methanol in the presence of ammonia and 0.5 g. of nickel at 90° and under 75 atmospheres. After filtration and concentration, the residue is purified by way of a silica gel column (system: chloroform/methanol 1:1). The product is taken up in sodium hydroxide solution and is acidified to pH 6 with acetic acid, thus yielding 715 mg. of 5-methulsulfonylamino-6-phenoxy-1-indanylamine as the acetate, m.p. 175°.

EXAMPLE 42

(a) 35 g. of 1-dimethylaminomethylene-5-nitro-6-phenoxyindan is agitated with 31 g. of hydroxylamine O-sulfonic acid in a mixture of 250 ml. of ether, 50 ml. of dioxane, and 250 ml. of water for 75 hours at 20°. After adding 100 ml. of water, the organic phase is separated, washed with water, dried, and concentrated. The residue is recrystallized from 2-propanol yielding 20 g. of 5-nitro-6-phenoxyindan-1-carbonitrile, m.p. 78°.

(b) 10 g. of this nitro compound is hydrogenated in 95 ml. of ethanol and 25 ml. of dioxane in the presence of 0.9 g. of palladium on charcoal (10%). Filtration, concentration, and recrystallization of the residue from diisopropyl ether yield 8 g. of 5-amino-6-phenoxyindan-1-carbonitrile, m.p. 108°.

(c) 1.72 g. of this amino compound is combined in 10 ml. of pyridine with 1.04 g. of methanesulfonic acid chloride at −2°. After 3 hours at 20°, the reaction mixture is concentrated, taken up in chloroform, the solution is washed with 1 N hydrochloric acid and water, dried, and concentration. Recrystallization of the residue from 2-propanol yields 1.54 g. of 5-methylsulfonylamino-6-phenoxyindan-1-carbonitrile, m.p. 110°.

EXAMPLE 43

3.58 g. of 5-methylsulfonylamino-6-phenoxy-2-phenylthio-1-indanone is dissolved in 35 ml. of methanol and 9 ml. of 1 N sodium hydroxide solution. At 5°, 680 mg. of sodium borohydride is added in incremental portions. After 16 hours at 20°, the pH is set to 8.2 with 22 ml. of 1 N hydrochloric acid, and the thus-precipitated crystallized product (3.50 g.) is vacuum-filtered. Chromatography over 120 g. of silica gel with chloroform yields initially 2.5 g. of cis-5-methylsulfonylamino-6-phenoxy-2-phenylthio-1-indanol, m.p. 135°.

EXAMPLE 44

3.2 g. of 5-methylsulfonylamino-6-phenoxy-1-indanol is agitated for 4 hours in 32 ml. of acetone with 0.6 g. of p-toluenesulfonic acid. After concentration under vacuum, the mixture is taken up in chloroform and chromatographed over 50 g. of silica gel. Initially, 1.47 g. of N-(6-phenoxy-5-indenyl)methanesulfonamide, m.p. 154°, and thereafter 0.27 g. of methanesulfonic acid N-(5-methylsulfonylamino-6-phenoxy-1-indenyl)amide, m.p. 194° are obtained.

EXAMPLE 45

(a) 47.3 g. of 5-fluoro-1-indanone is treated at 0° to −5° with 220 ml. of fuming nitric acid (3 hours). The mixture is poured on ice water, extracted with chloroform, and the chloroform phase is washed neutral and concentrated. Recrystallization of the residue from ethanol yields 20.4 g. of 5-fluoro-6-nitro-1-indanone, m.p. 89°.

(b) 20.3 g. of this compound is treated in 130 ml. of dimethyl sulfoxide for 3 hours at 50° with 9.8 g. of phenol and sodium bicarbonate. Concentration under vacuum, taking up of the residue in chloroform, washing with hydrochloric acid and sodium hydroxide solution, drying, concentrating, and recrystallization of the residue from ethanol yield 8.2 g. of 6-nitro-5-phenoxy-1-indanone, m.p. 103°.

(c) 10.2 g. of this compound is reduced as described in Example 29(c), thus obtaining 5.7 g. of 6-amino-5-phenoxy-1-indanone, m.p. 133°.

(d) 4.57 g. of this compound is reacted, as described in Example 29(d), with methanesulfonyl chloride, thus obtaining 5.9 g. of 6-methylsulfonylamino-5-phenoxy-1-indanone, m.p. 156°.

EXAMPLE 46

Analogously to Example 38, 6-methylsulfonylamino-5-phenoxy-1-indanone yields N-(1-hydroximino-5-phenoxy-6-indanyl)-methanesulfonamide, m.p. 200°.

EXAMPLE 47

Analogously to Example 37, 6-methylsulfonylamino-5-phenoxy-1-indanone yields 6-methylsulfonylamino-5-phenoxy-1-indano m.p. 156°.

EXAMPLE 48

Analogously to Example 44, 6-methylsulfonylamino-5-phenoxy-1-indanol yields N-(6-phenoxy-5-indenyl)-methanesulfonamide, m.p. 126°.

EXAMPLE 49

(a) 1.56 g. of 5-fluoro-6-nitro-1-indanone is treated in 28 ml. of dimethyl sulfoxide for 30 minutes at 20° with 0.8 g. of sodium bicarbonate and 0.88 g. of thiophenol. The mixture is concentrated under vacuum, the residue is taken up in chloroform, washed with hydrochloric acid and sodium hydroxide solution, dried, concentrated, and the residue is recrystallized from ethanol, yielding 1.27 g. of 6-nitro-5-phenylthio-1-indanone, m.p. 146°.

(b) 0.52 g. of this compound is reduced as described in Example 29(c), thus obtaining 153 mg. of 6-amino-5-phenylthio-1-indanone, m.p. 142°.

(c) 250 mg. of this compound is reacted with methanesulfonyl chloride as described in Example 29(d), thus producing 270 mg. of 6-methylsulfonylamino-5-phenylthio-1-indanone, m.p. 166°.

EXAMPLE 50

0.91 g. of N-(6-phenoxy-5-indanyl)methanesulfonamide is dissolved in 3 ml. of acetic acid and 0.72 ml. of acetic anhydride and combined, at 5°–10°, with a solution of 0.39 g. of chromium(VI) oxide in 0.3 ml. of water and 2 ml. of acetic acid. After 60 hours at 20°, the mixture is poured on water and the compound extracted with ethyl acetate. The solution is washed neutral and concentrated, resulting in a mixture of compounds. Chromatography over silica gel yields 0.47 g. of 5-methylsulfonylamino-6-phenoxy-1-indanone, m.p. 175°.

EXAMPLE 51

740 mg of 5-methylsulphonylamino-6-phenoxy-1-indanol, 7 ml of pyridine and 203 mg of acetyl chloride are stirred for 2 hours at 20° C. and for one hour at 60° C. After distilling off the pyridine, ice water is added, acidification is carried out with hydrochloric acid and extraction is effected with chloroform. Concentration of the chloroform solution and chromatography of the residue over 30 g of silica gel with chloroform initially produces 280 mg of N-acetyl-N-(1-acetoxy-6-phenoxy-5-indanyl)-methanesulphonamide having a melting point of 148° C. and then 200 mg of N-(1-acetoxy-6-phenoxy-5-indanyl)methanesulphonamide having a melting point of 70° C.

EXAMPLE 52

1.25 g of 5-amino-6-phenoxyindan-1-carbonitrile in 17 ml of methylene chloride are stirred for 16 hours at 20° C. with 1 g of triethylamine and 1.3 g of methanesulphonic acid anhydride. After concentrating, the residue is taken up in chloroform and the chloroform solution is washed with hydrochloric acid, water and sodium hydroxide solution. Concentration of the chloroform phase and recrystallisation of the residue from isopropanol/diisopropyl ether yields 1.49 g of 5-[bis(methylsulphonyl)amino]-6-phenoxyindan-1-carbonitrile having a melting point of 200° C.

The preceding examples can be repeated with similar success by substituting the generically and specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A compound of the formula

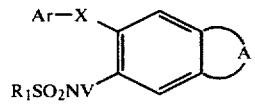

wherein
AR is phenyl, pyridyl, or phenyl or pyridyl substituted by halogen, alkyl of 1–4 carbon atoms or trifluoromethyl;
X is oxygen or sulfur;
$R_1$ is alkyl of 1–4 carbon atoms or alkyl of 1–4 carbon atoms substituted by fluorine or chlorine;
A is

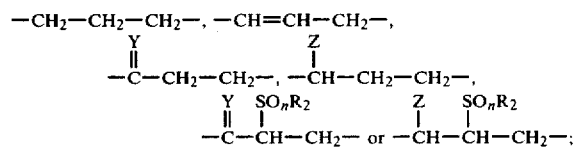

Y is oxo, oximino, $C_{1-4}$-alkoximino, phenylhydrazono or p-toluenesulfonylhydrazono; n is 0, 1 or 2; and $R_2$ is alkyl of 1–4 carbon atoms, phenyl or phenyl substituted by halogen, alkyl of 1–4 carbon atoms, nitro or carboxy; Z is hydroxy, acyloxy of 1 to 6 carbon atoms, $R_1SO_3$— wherein $R_1$ has the meaning given above, amino, acylamino of 1 to 6 carbon atoms, $R_1SO_2NH$— wherein $R_1$ has the meaning given above, or cyano, V is hydrogen, acyl of 1 to 6 carbon atoms or $R_1SO_2$— wherein $R_1$ has the meaning given above, and the salts thereof with physiologically acceptable bases or acids, wherein "acyl" in each case is a carboxylic acid acyl group.

2. A compound of claim 1 wherein AR is phenyl or phenyl substituted by halogen, alkyl of 1–4 carbon atoms or trifluoromethyl; and A is —CH₂—CH₂—CH₂—.

3. A compound of claim 1 wherein AR is phenyl or phenyl mono- or disubstituted by fluorine or chlorine.

4. A compound of claim 1 or 3 wherein $R_1$ is methyl.

5. A compound of claim 1 or 3 wherein Y is oxo.
6. N-(6-Phenoxy-5-indanyl)methanesulfonamide, a compound of claim 1.
7. N-[6-(4-Chlorophenoxy)-5-indanyl]methanesulfonamide, a compound of claim 1.
8. N-[6-(4-Tolyloxy)-5-indanyl]methanesulfonamide, a compound of claim 1.
9. N-[6-(4-Fluorophenoxy)-5-indanyl]methanesulfonamide, a compound of claim 1.
10. N-[6-(3-Trifluorophenoxy)-5-indanyl]methanesulfonamide, a compound of claim 1.
11. N-[6-(4-Chloro-2-methylphenoxy)-5-indanyl]methanesulfonamide, a compound of claim 1.
12. N-(6-Phenylthio-5-indanyl)methanesulfonamide, a compound of claim 1.
13. N-(6-Phenoxy-5-indanyl)trifluoromethanesulfonamide, a compound of claim 1.
14. N-(6-Phenylthio-5-indanyl)trifluoromethanesulfonamide, a compound of claim 1.
15. N-[6-(4-Fluorophenoxy)-5-indanyl]trifluoromethanesulfonamide, a compound of claim 1.
16. N-[6-(4-Chlorophenoxy)-5-indanyl]trifluoromethanesulfonamide, a compound of claim 1.
17. N-[6-(3-Chlorophenoxy)-5-indanyl]methanesulfonamide, a compound of claim 1.
18. N-(6-Phenoxy-5-indanyl)chloromethanesulfonamide, a compound of claim 1.
19. N-(6-Phenoxy-5-indanyl)ethanesulfonamide, a compound of claim 1.
20. N-[6-(2-Chlorophenoxy)-5-indanyl]methanesulfonamide, a compound of claim 1.
21. N-(6-Phenoxy-5-indanyl)methanesulfonamide, a compound of claim 1.
22. N-[6-(4-Chlorophenoxy)-5-indanyl]methanesulfonamide, a compound of claim 1.
23. N-[6-(4-Tolyloxy)-5-indanyl]methanesulfonamide, a compound of claim 1.
24. N-[6-(4-Fluorophenoxy)-5-indanyl]methanesulfonamide, a compound of claim 1.
25. N-[6-(3-Trifluoromethylphenoxy)-5-indanyl]methanesulfonamide, a compound of claim 1.
26. N-[6-(4-Chloro-2-methylphenoxy)-5-indanyl]methanesulfonamide, a compound of claim 1.
27. N-[6-(2-Chlorophenoxy)-5-indanyl]methanesulfonamide, a compound of claim 1.
28. N-[6-(3-Chlorophenoxy)-5-indanyl]methanesulfonamide, a compound of claim 1.
29. N-[6-(2-Fluorophenoxy)-5-indanyl]methanesulfonamide, a compound of claim 1.
30. N-[6-(2-Chloro-4-fluorophenoxy)-5-indanyl]methanesulfonamide, a compound of claim 1.
31. N-[6-(3,4-Dichlorophenoxy)-5-indanyl]methanesulfonamide, a compound of claim 1.
32. N-[6-(4-Bromophenoxy)-5-indanyl]methanesulfonamide, a compound of claim 1.
33. N-[6-(2,4-Dichlorophenoxy)-5-indanyl]methanesulfonamide, a compound of claim 1.
34. N-[6-(2-Tolyloxy)-5-indanyl]methanesulfonamide, a compound of claim 1.
35. N-[6-(3-Fluorophenoxy)-5-indanyl]methanesulfonamide, a compound of claim 1.
36. N-(6-Phenylthio-5-indanyl)methanesulfonamide, a compound of claim 1.
37. N-[6-(4-tert.-Butylphenylthio)-5-indanyl]methanesulfonamide, a compound of claim 1.
38. N-[6-(4-Fluorophenylthio)-5-indanyl]methanesulfonamide, a compound of claim 1.
39. N-[6-(4-Chlorophenylthio)-5-indanyl]methanesulfonamide, a compound of claim 1.
40. N-[6-(2-Pyridylthio)-5-indanyl]methanesulfonamide, a compound of claim 1.
41. N-[6-(4-Pyridylthio)-5-indanyl]methanesulfonamide, a compound of claim 1.
42. N-[6-(3-Pyridyloxy)-5-indanyl]methanesulfonamide, a compound of claim 1.
43. N-(6-Phenoxy-5-indanyl)trifluoromethanesulfonamide, a compound of claim 1.
44. N-(6-Phenylthio-5-indanyl)trifluoromethanesulfonamide, a compound of claim 1.
45. N-[6-(4-Fluorophenoxy)-5-indanyl]trifluoromethanesulfonamide, a compound of claim 1.
46. N-[6-(4-Chlorophenoxy)-5-indanyl]trifluoromethanesulfonamide, a compound of claim 1.
47. N-(6-Phenoxy-5-indanyl)chloromethanesulfonamide, a compound of claim 1.
48. N-(6-Phenoxy-5-indanyl)ethanesulfonamide, a compound of claim 1.
49. 5-Methylsulfonylamino-6-phenoxy-1-indanone, a compound of claim 1.
50. 6-(4-Chlorophenoxy)-5-methylsulfonylamino-1-indanone, a compound of claim 1.
51. 6-(4-Fluorophenoxy)-5-methylsulfonylamino-1-indanone, a compound of claim 1.
52. 6-(3-Chlorophenoxy)-5-methylsulfonylamino-1-indanone, a compound of claim 1.
53. 6-(2-Fluorophenoxy)-5-methylsulfonylamino-1-indanone, a compound of claim 1.
54. 5-Methylsulfonylamino-6-phenoxy-2-phenylthio-1-indanone, a compound of claim 1.
55. 5-Methylsulfonylamino-6-phenoxy-2-phenylsulfinyl-1-indanone, a compound of claim 1.
56. 5-Methylsulfonylamino-6-phenoxy-2-phenylsulfonyl-1-indanone, a compound of claim 1.
57. 5-Methylsulfonylamino-6-phenoxy-1-indanol, a compound of claim 1.
58. N-(1-Hydroximino-6-phenoxy-5-indanyl)methanesulfonamide, a compound of claim 1.
59. N-(1-Methoximino-6-phenoxy-5-indanyl)methanesulfonamide, a compound of claim 1.
60. N-[1-(4-Toluenesulfonylhydrazono)-6-phenoxy-5-indanyl]methanesulfonamide, a compound of claim 1.
61. 5-Methylsulfonylamino-6-phenoxy-1-indanylamine, a compound of claim 1.
62. 5-Methylsulfonylamino-6-phenoxyindan-1-carbonitrile, a compound of claim 1.
63. Cis-5-methylsulfonyl amino-6-phenoxy-2-phenylthio-1-indanol, a compound of claim 1.
64. N-(5-Phenoxy-6-indenyl)methanesulfonamide, a compound of claim 1.
65. 6-Methylsulfonylamino-5-phenoxy-1-indanone, a compound of claim 1.
66. N-(1-Hydroximino-5-phenoxy-6-indanyl)methanesulfonamide, a compound of claim 1.
67. 6-Methylsulfonylamino-5-phenoxy-1-indanol, a compound of claim 1.
68. N-(6-Phenoxy-5-indenyl)methanesulfonamide, a compound of claim 1.
69. 6-Methylsulfonylamino-5-phenylthio-1-indanone, a compound of claim 1.
70. A compound of claim 1 wherein "acyl" in each case is alkanoyl.
71. A pharmaceutical composition comprising an antiphlogistically effective amount of a compound of claim 1 and a pharmaceutically acceptable carrier.
72. An antiphlogistic composition comprising 1–250 mg of a compound of claim 1 and a pharmaceutically acceptable carrier.
73. A method of treating inflammation in a patient which comprises administering to the patient an amount of a compound of claim 1 effective to treat inflammation.

* * * * *